(12) United States Patent
Guo et al.

(10) Patent No.: US 11,927,584 B2
(45) Date of Patent: Mar. 12, 2024

(54) WATER HARDNESS DETECTION PROBE, SENSOR, DETECTION METHOD AND WATER SOFTENER

(71) Applicant: Shenzhen Angel Drinking Water Industrial Group Corporation, Guangdong (CN)

(72) Inventors: Min Guo, Guangdong (CN); Guoping Li, Guangdong (CN); Xue Xia, Guangdong (CN)

(73) Assignee: SHENZHEN ANGEL DRINKING WATER INDUSTRIAL GROUP CORPORATION, Guangdong (CN)

( * ) Notice: Subject to any disclaimer, the term of this patent is extended or adjusted under 35 U.S.C. 154(b) by 197 days.

(21) Appl. No.: 16/979,158

(22) PCT Filed: Sep. 24, 2019

(86) PCT No.: PCT/CN2019/107569
§ 371 (c)(1),
(2) Date: Sep. 8, 2020

(87) PCT Pub. No.: WO2020/220572
PCT Pub. Date: Nov. 5, 2020

(65) Prior Publication Data
US 2022/0042964 A1 Feb. 10, 2022

(30) Foreign Application Priority Data
Apr. 29, 2019 (CN) .......................... 201910353938.4

(51) Int. Cl.
*G01N 33/18* (2006.01)
*G01N 27/07* (2006.01)
*G01N 27/10* (2006.01)

(52) U.S. Cl.
CPC .......... *G01N 33/1853* (2013.01); *G01N 27/07* (2013.01); *G01N 27/10* (2013.01)

(58) Field of Classification Search
CPC ..... G01N 27/07; G01N 33/1853; G01N 27/10
(Continued)

(56) References Cited

U.S. PATENT DOCUMENTS

| 3,135,677 A | * | 6/1964 | Fischer | F24H 9/455 204/290.06 |
| 3,207,679 A | * | 9/1965 | Schmidt | C25D 11/26 205/333 |

(Continued)

FOREIGN PATENT DOCUMENTS

| CN | 2494985 Y | 6/2002 |
| CN | 105403254 A | 3/2016 |

(Continued)

OTHER PUBLICATIONS

Prentice, J. H., Journal of Dairy Research 1977, 44, 615-619. (Year: 1977).*

(Continued)

*Primary Examiner* — Arlen Soderquist
(74) *Attorney, Agent, or Firm* — Panitch Schwarze Belisario & Nadel LLP

(57) ABSTRACT

A water hardness detection probe, sensor, detection method and water softener are provided. The sensor includes a control unit which includes a processing module and a potential detection module. The detection probe includes a first probe and a second probe. When the first and second probes are both exposed in raw water, a potential between the first and second probes is regarded as first potential. When the first probe is in the raw water and the second probe is in softened water, the potential between the first and second probes is regarded as the second potential. The (Continued)

potential detection module measures the potential between the first and second probes. The processing module determines the water hardness of the softened water according to a difference between the first potential and the second potential. The sensor can detect the water hardness of the water softener in real time and eliminate detection deviations.

11 Claims, 4 Drawing Sheets

(58) Field of Classification Search
USPC .......................................................... 436/39
See application file for complete search history.

(56) References Cited

U.S. PATENT DOCUMENTS

| | | | | | |
|---|---|---|---|---|---|
| 3,213,004 | A | * | 10/1965 | Schmidt | C25D 5/34 |
| | | | | | 205/333 |
| 3,383,310 | A | * | 5/1968 | Ammer | G01N 33/1853 |
| | | | | | 324/443 |
| 3,463,707 | A | * | 8/1969 | Halker | C25D 9/06 |
| | | | | | 205/333 |
| 3,542,656 | A | * | 11/1970 | Aschenbrenner | C07C 51/36 |
| | | | | | 205/442 |
| 3,701,724 | A | * | 10/1972 | Entwhisle | C25B 11/093 |
| | | | | | 205/535 |
| 3,706,646 | A | * | 12/1972 | Gibson, Jr | C02F 5/08 |
| | | | | | 205/756 |
| 3,764,500 | A | * | 10/1973 | Gibson, Jr. | C02F 1/467 |
| | | | | | 205/349 |
| 3,773,555 | A | * | 11/1973 | Cotton | C25B 11/093 |
| | | | | | 427/226 |
| 3,778,307 | A | * | 12/1973 | Beer | C25B 11/091 |
| | | | | | 427/560 |
| 3,809,631 | A | * | 5/1974 | Ohta | C02F 1/463 |
| | | | | | 205/702 |
| 3,836,441 | A | * | 9/1974 | Millington | C25B 15/00 |
| | | | | | 205/322 |
| 3,935,082 | A | * | 1/1976 | Fritz | C25B 11/077 |
| | | | | | 205/333 |
| 3,957,613 | A | * | 5/1976 | Macur | G01N 27/403 |
| | | | | | 600/397 |
| 4,001,037 | A | * | 1/1977 | Beck | H01M 4/68 |
| | | | | | 429/188 |
| 4,019,970 | A | * | 4/1977 | Fritz | H01M 4/16 |
| | | | | | 205/333 |
| 4,040,939 | A | * | 8/1977 | Schenker | C25B 11/091 |
| | | | | | 427/126.3 |
| 4,123,341 | A | * | 10/1978 | Gnieser | G05D 21/02 |
| | | | | | 205/756 |
| 4,159,231 | A | * | 6/1979 | Smith | C25D 5/605 |
| | | | | | 205/333 |
| 4,320,010 | A | * | 3/1982 | Tucci | B01J 49/85 |
| | | | | | 210/96.1 |
| 4,326,943 | A | * | 4/1982 | Banziger | C25B 11/02 |
| | | | | | 204/290.13 |
| 4,384,941 | A | * | 5/1983 | Okamoto | C25B 9/73 |
| | | | | | 205/628 |
| 4,415,411 | A | * | 11/1983 | Kanai | C25B 11/04 |
| | | | | | 205/333 |
| 4,440,603 | A | * | 4/1984 | VanEffen | G01N 27/4168 |
| | | | | | 205/780 |
| 4,563,263 | A | * | 1/1986 | Oyama | G01N 27/3335 |
| | | | | | 204/418 |
| 4,692,226 | A | * | 9/1987 | Gimenez | C25B 3/25 |
| | | | | | 205/443 |
| 4,801,886 | A | * | 1/1989 | Steininger | G01N 27/4168 |
| | | | | | 324/438 |
| 4,839,007 | A | * | 6/1989 | Kotz | C02F 1/46109 |
| | | | | | 204/291 |
| 5,094,732 | A | * | 3/1992 | Oldani | B01D 61/44 |
| | | | | | 204/539 |
| 6,258,230 | B1 | * | 7/2001 | Shen | G01N 27/3272 |
| | | | | | 204/415 |
| 7,068,054 | B2 | | 6/2006 | Chedid et al. | |
| 2004/0055896 | A1 | * | 3/2004 | Anderson | C02F 1/4674 |
| | | | | | 204/263 |
| 2004/0104175 | A1 | * | 6/2004 | Rawson | B01J 49/85 |
| | | | | | 210/662 |
| 2005/0006237 | A1 | * | 1/2005 | Larkin | G01N 27/3335 |
| | | | | | 205/792 |
| 2006/0124453 | A1 | * | 6/2006 | Cross | C02F 1/46109 |
| | | | | | 204/260 |
| 2008/0237060 | A1 | * | 10/2008 | Hegel | C02F 1/645 |
| | | | | | 205/744 |
| 2009/0008268 | A1 | * | 1/2009 | Salathe | C02F 1/4674 |
| | | | | | 205/746 |
| 2010/0285151 | A1 | * | 11/2010 | Goldan | A61P 31/04 |
| | | | | | 424/662 |
| 2011/0042206 | A1 | * | 2/2011 | Tanahashi | C02F 1/4602 |
| | | | | | 204/278.5 |
| 2011/0139720 | A1 | * | 6/2011 | Soecknick | C02F 1/008 |
| | | | | | 210/687 |
| 2012/0216605 | A1 | * | 8/2012 | Silveri | G01N 27/08 |
| | | | | | 73/61.41 |
| 2013/0341200 | A1 | * | 12/2013 | McCormick | C25B 1/26 |
| | | | | | 205/345 |
| 2014/0124377 | A1 | * | 5/2014 | Joynt | C25B 1/26 |
| | | | | | 205/335 |
| 2015/0075999 | A1 | * | 3/2015 | Lammers | C25B 9/19 |
| | | | | | 204/263 |
| 2015/0196590 | A1 | * | 7/2015 | Sampson | A61K 45/06 |
| | | | | | 424/661 |
| 2015/0274558 | A1 | * | 10/2015 | McClean | C02F 1/72 |
| | | | | | 204/280 |
| 2016/0297691 | A1 | * | 10/2016 | Dopslaff | C02F 1/008 |
| 2016/0327416 | A1 | * | 11/2016 | Gagne | G01N 27/07 |
| 2017/0073246 | A1 | * | 3/2017 | Lian | G01N 33/1853 |
| 2017/0362093 | A1 | * | 12/2017 | Klingensmith | C02F 1/008 |
| 2018/0016164 | A1 | * | 1/2018 | Swartz | C02F 1/4674 |
| 2018/0170774 | A1 | * | 6/2018 | Xia | C02F 1/4674 |
| 2019/0210897 | A1 | * | 7/2019 | Justin | C02F 1/4602 |
| 2019/0302087 | A1 | * | 10/2019 | Kahn | C02F 1/42 |
| 2020/0062619 | A1 | * | 2/2020 | Swogger | C02F 1/4672 |
| 2022/0194819 | A1 | * | 6/2022 | Zhao | B01J 49/75 |

FOREIGN PATENT DOCUMENTS

| | | | | |
|---|---|---|---|---|
| CN | 107957439 | A | | 4/2018 |
| CN | 207301045 | U | | 5/2018 |
| DE | 19734209 | A1 | * | 2/1999 ............. C02F 1/465 |
| DE | 102014207224 | A1 | * | 10/2015 ............. C02F 1/76 |
| GB | 2028298 | A | * | 3/1980 ............. C02F 1/465 |
| GB | 2096642 | A | * | 10/1982 ......... C25B 11/0489 |
| JP | 49131282 | A | * | 12/1974 |
| JP | 04040284 | A | * | 2/1992 |
| JP | 09329580 | A | * | 12/1997 |
| JP | 2002090324 | A | * | 3/2002 |
| JP | 2008098159 | A | * | 4/2008 |

OTHER PUBLICATIONS

Lipp, L. et al, Hecrrochimico Acta 1997, 42, 1091-1099., (Year: 1997).*

Sardarinejad, A. et al, Sensors and Actuators A 2014, 214, 15-19. (Year: 2014).*

Bahdra, .S et al, Sensors and Actuators B 209, 2015, 803-810. (Year: 2015).*

Khuenpet, K. et al, Journal of Food Engineering 2017, 194, 67-78. (Year: 2017).*

Int'l Search Report dated Jan. 23, 2020 in Int'l Application No. PCT/CN2019/107569.

* cited by examiner

WATER HARDNESS DETECTION PROBE, SENSOR, DETECTION METHOD AND WATER SOFTENER

CROSS-REFERENCE TO RELATED APPLICATIONS

This application is a Section 371 of International Application No. PCT/CN2019/107569, filed Sep. 24, 2019, which has not yet published, which claims priority under 35 U.S.C. § 119(b) to Chinese Application No. 201910353938.4, filed Apr. 29, 2019, the disclosures of each of which are incorporated herein by reference in their entireties.

TECHNICAL FIELD

This invention relates to water quality detection systems, particularly relates to a water hardness detection probe, a sensor, a detection method and a water softener.

BACKGROUND

Water hardness refers to the content of calcium and magnesium ions (to be converted into calcium carbonate) in water, and hard water refers to the water with a high content of calcium and magnesium ions and is prone to form incrustation during the water using, particularly after being heated (calcium carbonate precipitation is formed, which is commonly known as incrustation). Water softener, common water hardness processing equipment, can reduce the water hardness by exchanging the calcium and magnesium ions in water with the use of ion exchange resin. The resin filled in the water softener will gradually become saturated with calcium and magnesium ions after disposing a certain quantity of water. After this procedure, the calcium and magnesium ions in the resin need to be exchanged and released with a saline solution (sodium chloride), which is called regeneration.

Existing water softeners are technologically imperfect, which is principally manifested by their incapableness in real-time monitoring and displaying of the outlet water hardness. Customers can only rely on the simple time-point reminding after factory settings or the experience and perception during the use of the water softeners to perform regeneration and maintenance of resins in the water softeners, thus resulting in unscientific, inconvenient and unreasonable usage of the water softeners and reducing the operating efficiency of the water softeners. The existing water softeners are inconvenient to use, low in maintenance efficiency, and poor in user experience due to their technological defects.

In the current water softeners, the water hardness of raw water is granted with a preset value, and the lifetime estimation of resin is based on the water productivity measuring from flow meter. The lifetime of resin is taken as a reference parameter for regeneration and maintenance of the water softeners. However, due to the significant difference of water quality among different user regions, this method cannot objectively indicate the saturation state of ion exchange resin for calcium and magnesium ions. Early regeneration of resin will cause the waste of water resources and salt, and the excessive discharge of salt will bring the environmental problems. Delayed regeneration of resin will result in the excessive failures of the resin and high water hardness production.

When detecting water hardness via instruments, the detection results obtained by different instruments may be drastically different, and the principal reason lies in the detection deviation caused by drifts and individual difference of the detection probe. The individual difference may be tiny, but will also affect the detection results. The primary cause of the drifts is the deposition of substances on the detection probes in water, and the gas bubbles in water may also influence the detection results. It still remains as an unsolved problem to eliminate the deviation generated from individual detection probes and drifts.

BRIEF SUMMARY OF THE DISCLOSURE

The invention provides a novel water hardness detection probe, a sensor, and a detection method. The water hardness can be displayed in real time through the cooperation of two probes and other elements.

An embodiment of the invention provides a water hardness detection probe which comprises a base part and a coating layer, wherein the coating layer is disposed on the surface of the base part, the base part is made of titanium, and the coating layer is made of ruthenium oxide-iridium oxide, lead oxide or tin oxide.

In one implementation of the invention, the probe further comprises a shell, wherein the shell is made of an insulating material and is located outside the coating layer.

In one implementation of the invention, the probe is connected to a pipe through a connector of a T-joint structure, a first terminal and a second terminal of the connector are used for connection to the pipe, the probe is inserted into a third terminal of the connector, and water in the connector contacts with the probe.

In one implementation of the invention, the coating layer has a thickness of 0.1-200 nm.

In one implementation of the invention, the detection probe comprises a first probe and a second probe; when the first probe and the second probe are both located in raw water, a potential value obtaining from a electrode pair of the first probe and the second probe is regarded as a first potential; and when the first probe is located in the raw water and the second probe is located in softened water, a potential value between the first probe and the second probe is regard as a second potential.

The embodiment of the invention further provides a sensor provided with the detection probe mentioned above. The sensor comprises the water hardness detection probe and a control module, wherein the control unit comprises a processing module and a potential detection module, the potential detection module measuring the potential between the first probe and the second probe; and the processing module determining water hardness of the softened water according to a potential difference between the first potential and the second potential.

In one implementation of the invention, the processing module determines the water hardness of the softened water according to the potential difference between the first potential and the second potential as well as a relational expression between the potential difference and the water hardness.

In one implementation of the invention, the relational expression is acquired through the following steps: acquiring multiple sets of potential differences between first potentials and second potentials and corresponding water hardness of the softened water; and fitting the potential differences and the water hardness to obtain the relational expression.

In one implementation of the invention, the control unit further comprises a pre-processing module, wherein the potential detection module is connected to the pre-processing module, and the pre-processing module is connected to the processing module; and the pre-processing module performs pre-processing on the first potential and the second potential, and the pre-processing comprises impedance transformation matching, linear amplification, level shifting and/or noise processing.

In one implementation of the invention, the control unit further comprises a regeneration module connected to the processing module and a regeneration system of a water softener.

In one implementation of the invention, the sensor further comprises a display unit which is connected to the control unit.

In one implementation of the invention, the sensor further comprises a raw water pipe, a softened water pipe and a converging pipe, wherein the raw water pipe and the softened water pipe are communicated with the converging pipe respectively; a first valve is located on the raw water pipe, and the first probe communicated with the raw water pipe is disposed between the first valve and an outlet of the raw water pipe; a second valve is disposed on the softened water pipe; the second probe communicated with the converging pipe is disposed on the converging pipe; and the first valve and the second valve are connected to the control unit respectively.

The embodiment of the invention further provides a water hardness detection method adopting the sensor mentioned above. The water hardness detection method comprises: opening the first valve, closing the second valve, injecting raw water into the raw water pipe, locating both the first probe and the second probe in the raw water, measuring a potential difference between the first probe and the second probe as a first potential; opening the second valve, closing the first valve, injecting softened water into the softened water pipe, and locating the first probe in the raw water, locating the second probe in the softened water, and measuring a potential difference between the first probe and the second probe as a second potential; and determining, by the processing module, the water hardness of the softened water according to the potential difference between the first potential and the second potential.

In one implementation of the invention, the method further comprises:

performing pre-processing on the first potential and the second potential; and inputting into the processing module the first potential and the second potential after being subjected to the pre-processing;

wherein the pre-processing comprises impedance transformation matching, linear amplification, level shifting and/or noise processing.

In one implementation of the invention, the method further comprises: turning on, by the control unit, the regeneration system of the water softener through the regeneration module if the water hardness reaches a preset value.

In one implementation of the invention, the method further comprises: displaying the water hardness of the softened water by the display unit.

The embodiment of the invention further provides a water softener adopting the sensor mentioned above.

According to the water softener, the raw water pipe is connected to a main raw water pipe of the water softener, the softened water pipe is connected to a main softened water pipe of the water softener, and the converging pipe is connected to a drain outlet of the water softener.

The water hardness detection probe of the invention can accurately detect monovalent and divalent ions in water; the chemical environment influences the potential of the probe, and different species and concentrations of ions induce a potential change between the two probes; one probe is alternately exposed in raw water and softened water, so that the potential between the two probes varies, and the sensor can calculate the water hardness of the softened water according to the potential variation, so that real-time monitoring of the outlet water hardness of the water softener is achieved. By adoption of the detection probe, the sensor and the detection method of the invention, when the water softener detects the water hardness, detection deviation caused by drifts of the detection probe can be avoided, particularly, the individual discrepancies of the probes from the same model are eliminated, the detection disturbance is prevented from substances deposition on the probe and the gas bubbles in the water, and meanwhile, deviations generated by different detection probes and drifts are eliminated.

DETAILED DESCRIPTION OF EMBODIMENTS

To achieve a better understanding of the solutions and numerous advantages of the invention, a more detailed description of specific implementations of the invention is provided below in connection with the accompanying drawings and embodiments. However, the following specific implementations and embodiments used herein are for the purpose of describing particular implementations and embodiments by way of example only and are not intended to be limiting the scope of the claimed invention in any manner.

Unless otherwise clearly specified or defined, the term "connect" in the description of the invention should be broadly understood, for example, it may refer to direct connection or indirect connection through an intermediate medium. It should be declared that these terms such as "upper", "lower", "front", "back", "left" and "right" involved in the description of the invention are used to indicate any directional or positional relations based on the accompanying drawings to simplify the description of the invention. These terms do not indicate or imply that the devices or elements referred must retain specific directions or must be configured and operated in specific directions, and thus, should not be construed as limitations of the invention.

Figure 1:
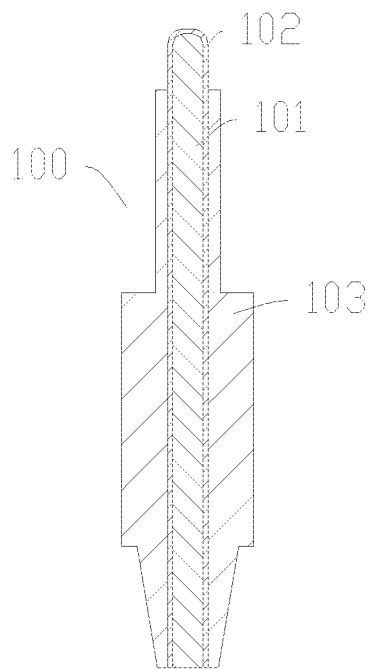
FIG. 1 is a schematic diagram of a water hardness detection probe of the invention.

As shown in FIG. 1, this embodiment provides a water hardness detection probe 100 which comprises a base part 101 and a coating 102. The base part 101 is made from titanium and the coating 102, which is disposed on the surface of the base part 101, is made from ruthenium oxide-iridium oxide, lead oxide or tin oxide, wherein the ruthenium oxide-iridium oxide, the lead oxide and the tin oxide are all existing materials. The thickness of the coating 102 is 0.1-200 nm, and is preferably 1-100 nm.

The probe 100 may further comprise a shell 103, which is made from an insulating material and is located outside the coating 102. The probe 100 has a detection terminal and a wiring terminal, wherein the wiring terminal may be connected to a wire. In this embodiment, the probe 100 can easily detect monovalent and divalent ions in water, wherein the monovalent ions are typically K and Na ions, and the divalent ions are typically Ca and Mg ions. The probe 100 can quickly and sensitively respond to a potential signal, thereafter indicate the water hardness of softened water in a water softener by certain calculation.

The shape of probe 100 may be cylindrical, columnar or needle-type, and the invention has no limitation on the shape of the probe 100. The size of the probe 100 is determined as the case may be. For example, but not limited to, if the probe 100 is cylindrical, the diameter of the detection terminal of the probe 100 is 5 mm.

Figure 2:
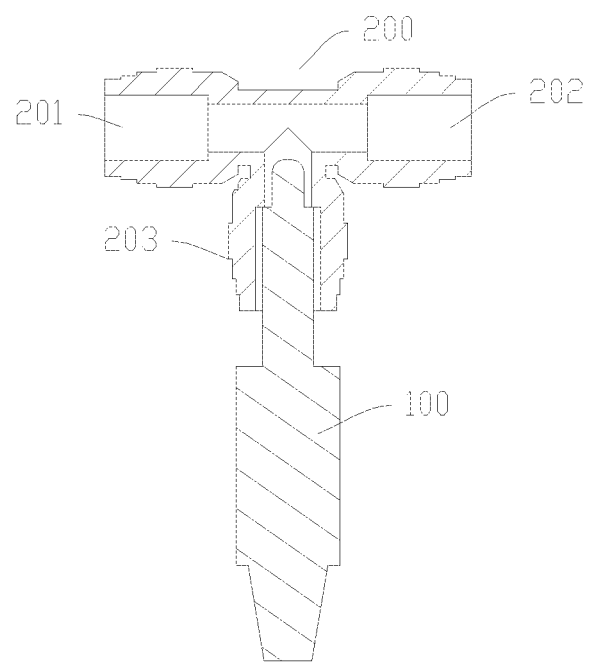
FIG. 2 is a schematic diagram of a connector of the water hardness detection probe of the invention.

As shown in FIG. 2, the probe 100 can be connected to a pipe supported by a connector 200. The connector 200 displays a "T-joint" structure, wherein the first terminal 201 and the second terminal 202 of the connector 200 are connected to the pipeline and the detection terminal of the probe 100 is inserted into the third terminal 203 so that water in the pipe can flow through the connector 200 and can be detected by the probe 100.

Figure 3:
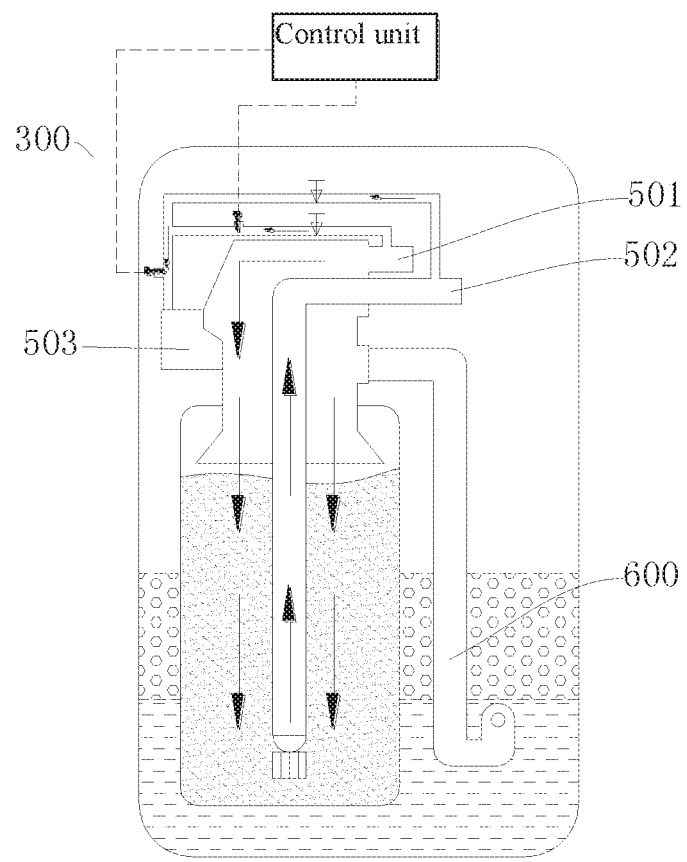
FIG. 3 is a schematic diagram of a water softener of the invention.
Figure 4:
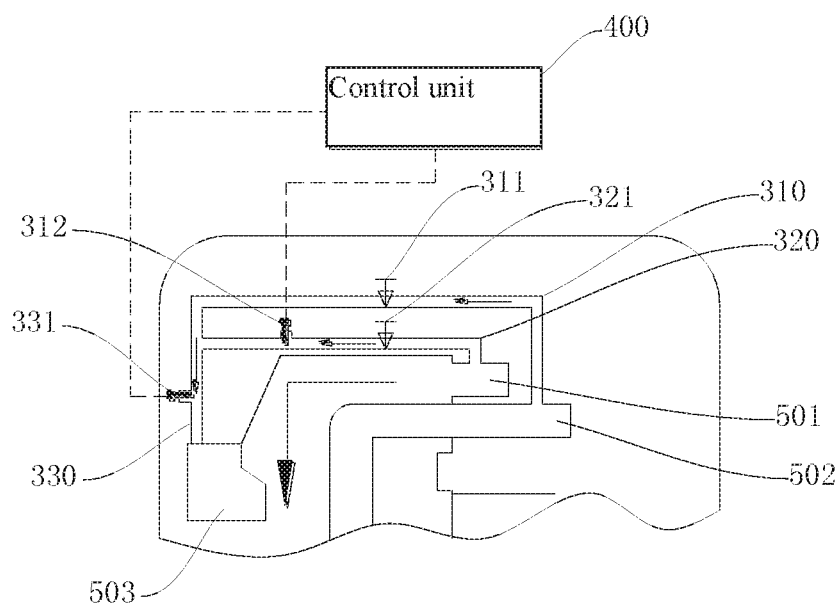
FIG. 4 is a schematic diagram of a sensor of the invention.

As shown in FIG. 3 and FIG. 4, this embodiment provides a sensor 300 which can detect water hardness with the assistance of the detection probe described above. The detection probe includes a first probe 312 and a second probe 331, wherein the two probes are of the same model. As both of the first probe 312 and the second probe 331 are located in water, a potential will be obtained from the first probe 312 and the second probe 331. Even though the first probe 312 and the second probe 331 are located in the same water, a slight potential will be formed between the first probe 312 and the second probe 331 because the first probe 312 and the second probe 331 are not entirely identical.

When the sensor 300 is applied to a water softener, if the first probe 312 and the second probe 331 are both located in raw water, the potential between the first probe 312 and the second probe 331 is a first potential; and if the first probe 312 is located in raw water and the second probe 331 is located in softened water, the potential between the first probe and the second probe is a second potential.

Figure 5:
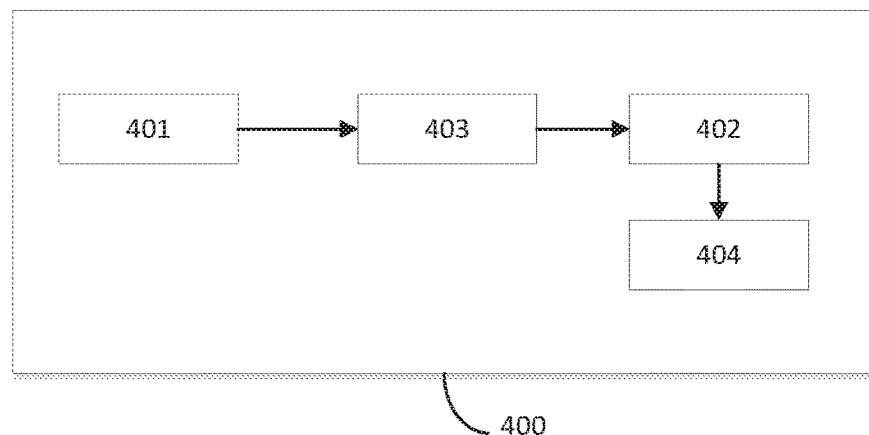
FIG. 5 is a schematic diagram of a control unit of the invention.

The sensor 300 further comprises a control unit 400, as shown in FIG. 5, which comprises a potential detection module 401 and a processing module 402.

The first probe 312 and the second probe 331 are connected to the potential detection module 401, therefore the potential between the first probe 312 and the second probe 331 can be detected by the potential detection module 401. Then, the control unit 400 can measure the first potential and the second potential by means of the potential detection module 401.

In this embodiment, the processing module 402 may include a MCU for data calculating and processing. The processing module 402 determines the water hardness of softened water based on the variation between the first potential and the second potential.

Optionally, the sensor 300 comprises a raw water pipe 310, a softened water pipe 320 and a converging pipe 330. The raw water pipe 310 and the softened water pipe 320 are connected to the converging pipe 330 respectively, and both of the raw water, passing through the raw water pipe 310, and softened water, passing through the softened water pipe 320, will flow through the converging pipe 330. Electromagnetic valves are disposed on the raw water pipe 310 and the softened water pipe 320 to enable or block respective water flow, thereafter the pipes can be effectively controlled to prevent any water backflow, as the backflow may affect the detection precision. The control unit 400 controls the operation of the sensor 300. Arrows in FIG. 3 and FIG. 4 represent the water flow direction.

A first valve 311 is disposed on the raw water pipe 310 to enable or block the raw water flow through the raw water pipe 310. A second valve 321 is disposed on the softened water pipe 320 to enable or block the softened water flow through the softened water pipe 320. The first valve 311 and the second valve 321 are connected to the control unit 400 respectively, thus the control unit 400 controls the first valve 311 and the second valve 321 to switch on or off.

A first probe 312 is disposed on the raw water pipe 310 and is located between the first valve 311 and the outlet of raw water pipe 310. The first probe 312 can be connected to the raw water pipe 310 through a connector 200 to communicate with the raw water pipe 310, thus, the first probe 312 can detect the water in the raw water pipe 310.

A second probe 331 is disposed on the converging pipe 330 and can be connected to the converging pipe 330 through a connector 200 to communicate with the converging pipe 330, thus, the second probe 331 can detect the water in the converging pipe 330.

When the first valve 311 is switched on and the second valve 321 is switched off, the raw water (untreated water) in the water softener flows into the converging pipe 330 from the raw water pipe 310. During this procedure, the first probe 312 and the second probe 331 are both located in the raw water, and the potential between the first probe 312 and the second probe 331 is measured as the first potential.

When the first valve 311 is switched off and the second valve 321 is switched on, the softened water in the water softener flows into the converging pipe 330 from the softened water pipe 320. During this procedure, the first probe 312 is located in the raw water whereas the second probe 331 is located in the softened water, therefore the potential between the first probe 312 and the second probe 331 is measured as the second potential.

In this processing described above, the first probe 312 is always located in the raw water, and the second probe 331 is firstly located in the raw water and secondly located in the softened water. As the environment, wherein the second probe 331 is located, is variable, the first potential and the second potential are also variable, and the variation between the first potential and the second potential can reflect the water hardness of the softened water. The control unit 400 can measure the water hardness of the softened water according to the first potential and the second potential.

In the traditional detection methods, the variation between traditional detection probes and environmental influences may result in large deviations of detection results. In this invention, the two detection probes are initially located in the same water environment, then only the second probe is located in an altered water environment, so that the detection deviations caused by product discrepancies and position shifts of the first probe and the second probe can be eliminated, thus ensuring that the detection results are more accurate than before.

As shown in FIG. 3, in the water softener, the sensor 300 is connected to a pipe of the water softener. The raw water pipe 310 is connected to a main raw water pipe 501 of the water softener, the softened water pipe 320 is connected to a main softened water pipe 502 of the water softener, and the converging pipe 330 is connected to a drain outlet 503 of the water softener. Water in the converging pipe 330 is discharged via the drain outlet 503.

Optionally, a relational expression between the potential difference mentioned above and the water hardness is stored in the processing module 402. During the determination of the relational expression between the potential difference and water hardness, a large number of the potential difference value and corresponding water hardness value of the softened water are collected and fitted to figure out of the relational expression. After acquiring the difference, the processing module 402 determines the water hardness of the softened water according to the relational expression.

As an advanced embodiment, the control unit 400 may further comprise a pre-processing module 403, wherein the potential detection module 401 is connected to the pre-processing module 403, and the pre-processing module 403 is connected to the processing module 402. The pre-processing module 403 firstly performs pre-processing on the potential difference signal, which is captured by the potential detection module 401 from the first probe 312 and the second probe 331, and secondly send the pre-processed signal to the processing module 402 for further calculation.

Figure 6:
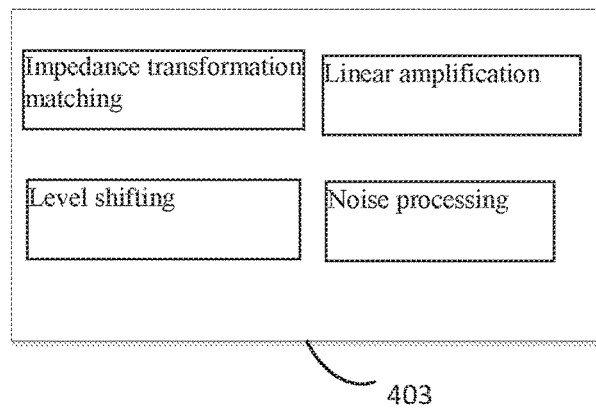
FIG. 6 is a schematic diagram of a pre-processing module of the invention.

As shown in FIG. 6, the pre-processing module 403 comprises an impedance transformation matching sub-module, a linear amplification sub-module, a level shifting sub-module and a noise processing sub-module. The pre-processing procedure of the pre-processing module 403 includes impedance transformation matching, linear amplification, level shifting and noise processing, which can be sequentially managed. The parameters of the sub-modules described above can be arranged differently according to the actual conditions. For example, the impedance transformation matching parameter is 100, the linear amplification factor is 10-30, the level shifting parameter is 1.5V, the noise processing is low-pass filtering and the cut-off frequency is 1000 Hz.

Optionally, the control unit 400 further comprises a regeneration module 404, wherein the regeneration module 404 is connected to the processing module 402 and a regeneration system 600 of the water softener. If the water hardness, calculated by the processing module 402, of the softened water reaches a preset value (such as 120 ppm), a starting signal will be sent to the regeneration module 404, which subsequently controls the generation system 600 to launch regeneration and maintenance of the ion exchange resin in the water softener.

Figure 7:
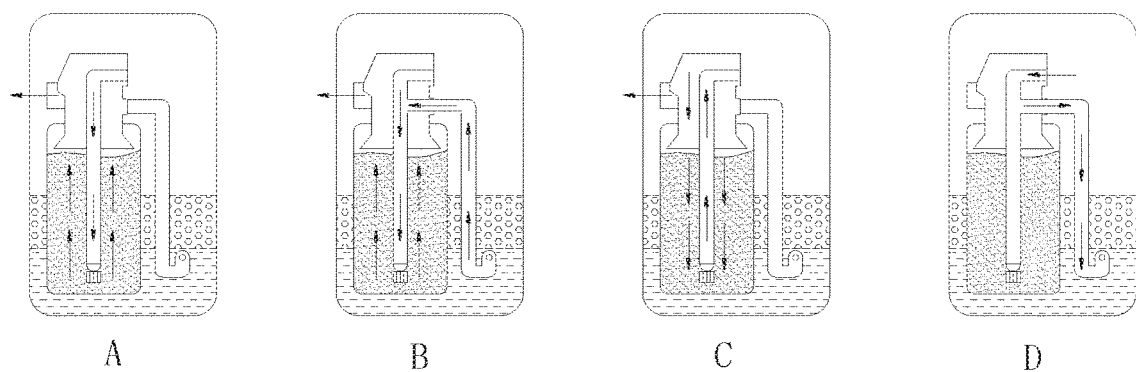
FIG. 7 is a schematic diagram of a regeneration process of the invention.

As shown in FIG. 7, the operation process of the regeneration system 600 comprises:

A. Backward-flushing: water enters the water softener via a softened water outlet to back-flush the resin, after which the waste water is discharged via the drain outlet.

B. Slow-washing by absorbed salt: saline water is absorbed into the main softened water pipe to wash the resin.

C. Forward flushing: water enters the water softener via the raw water inlet to flush the resin and the saline water in the pipe.

D. Water supplement: the regeneration system 600 is supplemented with the saline water.

The sensor in this embodiment may further comprise a display unit (not shown), wherein the display unit is connected to the control unit 400 to display the water hardness of the softened water as well as the operation status of the sensor in real time. The display unit may be a monitor of the water softener.

This embodiment further provides a water hardness detection method using the sensor described above. The water hardness detection method comprises the following steps:

1. Primary detection: with the first valve 311 on and the second valve 321 off, the raw water from the raw water pipe 310 will flow through the converging pipe 330 and be subsequently discharged via the drain outlet 503. Since both of the first probe 312 and the second probe 331 are located in the raw water, the potential between these two probe is detected as a first potential;

2. Secondary detection: with the second valve 321 on and the first valve 311 off, the softened water from the softened water pipe 320 will flow through the converging pipe 330 and be subsequently discharged via the drain outlet 503. Since the first probe 312 is located in the raw water and the second probe 331 is located in the softened water, the potential between these two probes is detected as a second potential;

3. The control unit 400 acquires the first and the second potential signals, after which the processing module determines the water hardness of the softened water according to the variation between the first and the second potential.

The discrepancy between the first probe 312 and the second probe 331 and environmental influences may lead to deviations of the final detection results. The two probes are located in same water environment during primary detection whereas in different water environments during secondary detection. Thus, the test deviations caused by product discrepancies and position shifts of the detection probes can be eliminated by subtracting the first potential from the second potential.

In Step 1 and Step 2 described above, the first and the second potential are detected by the potential detection module 401 of the control unit. The processing module 402 determines the water hardness of the softened water according to the difference between the first and the second potential as well as the relational expression between the difference and the water hardness.

If the first potential obtained during primary detection is 10 mV and the second potential obtained during secondary detection is 30 mV, the difference between the first potential and the second potential will be 20 mV. Therefore, the water hardness will be 100 ppm according to the relational expression.

Optionally, the first and second potential signals are input to the processing module for AD conversion by a 12-bit AD converter. Subsequently, the difference between the first and the second potential is calculated, after which a functional processing is performed, according to the relational expression, to obtain the outlet water hardness of the water softener.

The relational expression can be obtained by big data processing as follows:

With numerous difference values between the first and second potential as well as the corresponding water hardness values of the softened water, the differences and the water hardness are fitted to obtain a relational expression: $y=f(x)$.

For example, the relational expression obtained by fitting a large amount of data is as follows:

$Y=A\times(-2.4395x^3+5.3328x^2-3.9047x+1)$, wherein A is the hardness of the raw water, x is a ratio of the difference signal value to a reference value (x is within 0-1), the reference value is in direct proportion to the hardness of the raw water and y is the water hardness of the softened water.

Reference value=8A/3 and the reference value is preferably 500-1000. The hardness A of the raw water can be obtained by actual measurement.

For example, if the hardness A of the raw water is 300 ppm and the reference value is set as 800:

When the difference signal value is 80 and x=0.1, it can be figured out that the calculated outlet water hardness is 198 ppm. Thus, the deviation between the calculated result and the result, 190 ppm, measured by an atomic absorption spectrum ICP instrument is merely 4.5%;

When the differential signal value is 160 and x=0.2, it can be figured out that the calculated outlet water hardness is 124 ppm. Thus the deviation between the calculated result and the result, 118 ppm, measured by the atomic absorption spectrum ICP instrument is merely 4.8%;

When the differential signal value is 400 and x=0.5, it can be figured out that the calculated outlet water hardness is 23 ppm. Thus, the deviation between the calculated outlet water hardness and the result, 24 ppm, measured by the atomic absorption spectrum ICP instrument is merely 4.3%.

Figure 8:
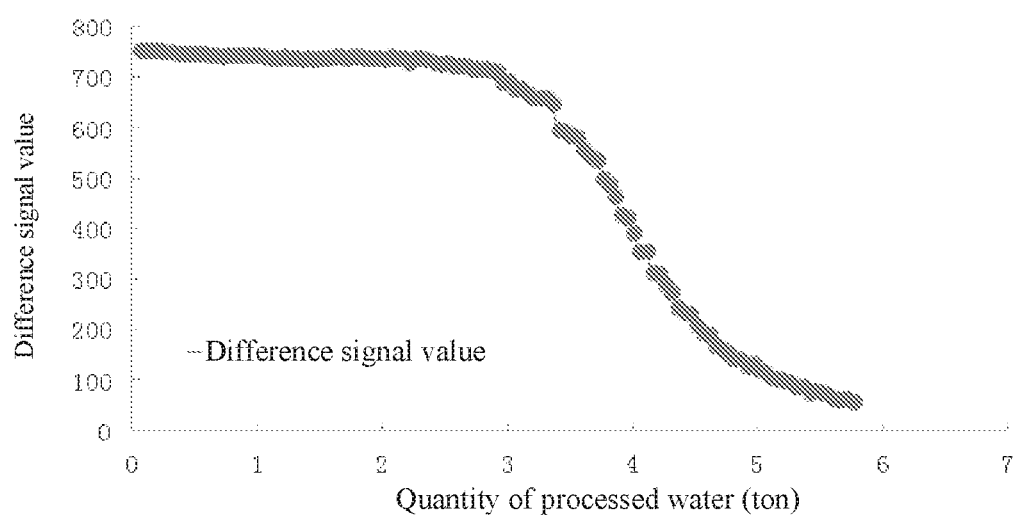
FIG. 8 is a variation chart of the quantity of water processed by the water softener and a differential signal value.

FIG. 8 shows the quantity values of processed water by the water softener as well as the difference signal values. The variation of the difference signal values is consistent with the variation of the softening resin operation status. The initial processing efficiency of the resin is the highest, and correspondingly, the difference signal value is high and stable. After processing a certain quantity of water, an inflection point appears, which indicates that the efficiency of the resin is decreasing. With the increasing quantity of processed water, the hardness of the softened water is increasing constantly, during which the increase trend becomes faster and faster and the difference signal value decreases accordingly. When the resin is saturated, the difference signal value becomes stable and reaches the lower limit.

Optionally, the first and the second potential are input to the processing module after being pre-processed by the pre-processing module. The pre-processing includes impedance transformation matching, linear amplification, level shifting and noise processing. A pre-processed signal is input to the processing module for AD conversion by a 12-bit AD converter. Subsequently, the difference between the first and the second potential is calculated, after which a functional processing is performed according to the relational expression to obtain the outlet water hardness of the water softener.

According to the method in this embodiment, when the water hardness of the softened water reaches a preset value, the control unit will launch the regeneration system 600 of the water softener through the regeneration module 404. The regeneration system 600 carries out regeneration and maintenance of the ion exchange resin in the water softener.

The water hardness obtained by the processing module can be sent to the display unit, and the real-time water hardness of the softened water is displayed by the display unit.

According to the sensor in this embodiment, a initial detection time, a secondary detection time and a detection time interval can be adjusted according to the probe stability and operating environment. For example, both the initial detection time and the secondary detection time can be set from 10 s to 60 s, and a complete detection cycle composes of one initial detection process and one secondary detection process. The detection cycle will be started at an interval to achieve continuous detection. The time interval can be set as required.

In this embodiment, only one set of probes is used, and the structural configuration of multiple probes sets is avoided, so that detection deviations are minimized. The probes have high safety and reliability and good stability. The location and structure of the probes of the invention simplify the pipeline design, reduce the cost, and effectively improve the detection stability. The probes are of a quick-fit structure, thus being easy to maintain, detect and replace.

According to the sensor in this embodiment, pipeline flushing and automatic elimination of factors that may cause deviations are synchronously completed every time measurement is started, so that the application of equipment and devices is simplified, a reference electrode is not needed, and the result of the current test will not be affected by the previous test.

This embodiment further provides a water hardness detection system which detects water hardness by means of the detection probe mentioned above. The detection probes include a first probe 312 and a second probe 331, wherein the first probe 312 and the second probe 331 are of the same model, and when the first probe 312 and the second probe 331 are both exposed in water, there is a potential between the first probe 312 and the second probe 331. Even if the first probe 312 and the second probe 331 are in the same water, there is a tiny potential fluctuation between the first probe 312 and the second probe 331 because the first probe 312 and the second probe 331 are not entirely identical.

When the detection system is applied to the water softener, if the first probe 312 and the second probe 331 are both exposed in raw water, the potential between the first probe 312 and the second probe 331 is regarded as the first potential; and if the first probe 312 is in raw water and the second probe 331 is in softened water, the potential between the first probe and the second probe is regarded as the second potential.

The detection system further comprises a control unit 400 which, as shown in FIG. 5, comprises a potential detection module 401 and a processing module 402.

The first probe 312 and the second probe 331 are connected to the potential detection module 401, the potential between the first probe 312 and the second probe 331 is detected by the potential detection module 401, and the control unit 400 determines the first potential and the second potential by means of the potential detection module 401.

In this embodiment, the processing module 402 may include a MCU for data processing. The processing module 402 determines the water hardness of the softened water according to the potential difference between the first potential and the second potential.

Optionally, the detection system further comprises a raw water pipe 310, a softened water pipe 320 and a converging pipe 330. The raw water pipe 310 and the softened water pipe 320 are connected to the converging pipe 330 respectively, and raw water from the raw water pipe 310 and softened water from the softened water pipe 320 both flow through the converging pipe 330. Electromagnetic valves are disposed on the raw water pipe 310 and the softened water pipe 320 to switch on/off the water flow in raw water pipe 310 and softened water pipe 320 respectively, and the pipes can be effectively controlled to open or close to prevent liquid from flowing backwards, which may otherwise affect the detection accuracy. The control unit 400 controls the operation of the water hardness detection system.

A first valve 311 is disposed on the raw water pipe 310 to switch on/off the flow of the raw water in raw water pipe 310. A second valve 321 is disposed on the softened water pipe 320 to switch on/off the flow of the softened water in softened water pipe 320. The first valve 311 and the second valve 321 are connected to the control unit 400 respectively, and the control unit 400 controls the first valve 311 and the second valve 321 to open or close.

The first probe 312 is disposed on the raw water pipe 310 and is located between the first valve 311 and the outlet of raw water pipe 310. The first probe 312 can be connected to the raw water pipe 310 through a connector 200, that is, the first probe 312 can contact with water in the raw water pipe 310.

The second probe 331 is disposed on the converging pipe 330 and can be connected to the converging pipe 330 through the connector 200, that is, the second probe 331 can contact with water in the converging pipe 330.

When the first valve 311 is open and the second valve 321 is closed, raw water (untreated water) in the water softener flows into the converging pipe 330 from the raw water pipe 310. At this moment, the first probe 312 and the second probe 331 are both exposed in the raw water, and a potential between the first probe 312 and the second probe 331 is taken as the first potential.

When the first valve 311 is closed and the second valve 321 is open, softened water generated from the water softener flows into the converging pipe 330 from the softened water pipe 320. At this moment, the first probe 312 is in the raw water, the second probe 331 is in the softened water, and a potential between the first probe 312 and the second probe 331 is taken as the second potential.

In this process, the first probe 312 is always exposed in the raw water, and the second probe 331 is exposed in the raw water initially and then is exposed in the softened water; and the first potential and the second potential are different because of the variable chemical environment of the second probe 331, and the potential difference between the first potential and the second potential can indicate the water hardness of the softened water. The control unit 400 determines the water hardness of the softened water according to the first potential and the second potential.

The difference between traditional detection probes and environmental impacts may incur great deviations in detection results. In the application, the two detection probes are exposed in the same water environment initially, and then the water environment of second probe is changed, so that deviations of detection results caused by production discrepancies and drifts of the first probe and the second probe can be eliminated, thus ensuring that the detection results are more accurate.

As shown in FIG. 3, in the water softener, the water hardness detection system is connected to a pipe of the water softener. The raw water pipe 310 is connected to a main raw water pipe 501 of the water softener, the softened water pipe 320 is connected to a main softened water pipe 502 of the water softener, and the converging pipe 330 is connected to a drain outlet 503 of the water softener. Water in the converging pipe 330 is discharged via the drain outlet 503.

Optionally, a relational expression between the potential difference and the water hardness is stored in the processing module 402. For the determination of the relational expression between the potential difference and the water hardness, a large number of data about potential differences and the corresponding water hardness in the softened water are collected and fitted to obtain the relational expression. After acquiring the data of potential difference, the processing module 402 determines the water hardness of the softened water according to the relational expression.

As a preferred solution, the control unit 400 further comprises a pre-processing module 403, wherein the potential detection module 401 is connected to the pre-processing module 403, and the pre-processing module 403 is connected to a processing module 402. The pre-processing module 403 performs pre-processing on potential signals of the first probe 312 and the second probe 331 acquired by the potential detection module 401, and the processed signal is sent to the processing module 402 for calculation.

As shown in FIG. 6, the pre-processing module 403 comprises an impedance transformation matching sub-module, a linear amplification sub-module, a level shifting sub-module and a noise processing sub-module. The pre-processing of the pre-processing module 403 includes impedance transformation matching, linear amplification, level shifting and/or noise processing, which are sequentially performed on the signal. Parameters of the sub-modules can be set according to the practical condition. For example, the impedance transformation matching parameter is 100, the linear amplification factor is 10-30, the level shifting parameter is 1.5V, the noise processing is low-pass filtering, and the cut-off frequency is 1000 Hz.

Optionally, the control unit 400 further comprises a regeneration module 404, wherein the regeneration module 404 is connected to the processing module 402 and a regeneration system 600 of the water softener. When the water hardness of the softened water, acquired by the processing module 402, reaches a preset value (such as 120 ppm), a starting signal is sent to the regeneration module 404, which turns on the generation system 600 to conduct regeneration and maintenance on ion exchange resin in the water softener.

The sensor in this embodiment may further comprise a display unit (not shown), wherein the display unit is connected to the control unit 400 and displays the water hardness of the softened water and the operating state of the sensor in real time, and the display unit can be a display of the water softener.

It should be noted that the embodiments described above with reference to the accompanying drawings are merely used to explain the invention, and are not intended to limit the scope of the invention. Those ordinarily skilled in the art would appreciate that any modifications or equivalent substitutions made to the invention without departing from the spirit and scope of the invention should also fall within the scope of the invention. In addition, unless otherwise specified in the context, any terms in the singular form may also be in the plural form, vice versa. Moreover, unless otherwise particularly stated, one part or all of any embodiment may be combined with one part or all of another embodiment for use.

What is claimed is:

1. A sensor comprising:
   a water hardness detection probe comprising a first probe and a second probe, and used for measuring a potential difference between the first probe and the second probe; wherein each of the first probe and the second probe comprises a base part and a coating layer, the coating layer is deposited on all surfaces of the base part, the base part is made of titanium, and the coating layer is made of ruthenium oxide-iridium oxide, lead oxide or tin oxide;
   a raw water pipe, wherein a first valve is located on the raw water pipe, and the first probe is connected to the raw water pipe and disposed between the first valve and an outlet of the raw water pipe;
   a softened water pipe, wherein a second valve is located on the softened water pipe, a converging pipe, communicating with the raw water pipe and the softened water pipe respectively, wherein the second probe is disposed on the converging pipe; and a controller, comprising a processor and a potential detector configured to measure a potential between the first probe and the second probe, wherein the controller connects to the first valve and the second valve respectively;

wherein during detecting water hardness of softened water, the first probe is configured to being located in raw water and the second probe is configured to being located in the raw water firstly and then being transferred into the softened water; when the first probe and the second robe are both located in the raw water a first potential value obtained b the potential detector is regarded as a first potential, and when the first probe is located in the raw water and the second probe is located in the softened water, a second potential value obtained by the potential detector is regarded as a second potential; and the processor is configured to determine the water hardness of the softened water according to a potential difference between the first potential and the second potential.

2. The sensor of claim 1, wherein the controller further comprises a pre-processor, the potential detector is connected to the pre-processor, and the pre-processor is connected to the processor; and the pre-processor is configured to perform pre-processing on the first potential and the second potential, and the pre-processing comprises impedance transformation matching, linear amplification, level shifting and/or noise processing.

3. The sensor of claim 1, wherein the controller is further configured to be connected to a regeneration system of a water softener to control regeneration and maintenance of ion exchange resin in the water softener.

4. The sensor of claim 1, further comprising a displayer connected to the controller.

5. The sensor of claim 1, wherein each of the first probe and the second probe further comprises a shell being made of an insulating material and being located outside at least a portion of the coating layer.

6. The sensor of claim 1, wherein the first probe is connected to the raw water pipe through a first connector of a T-joint structure, and the second probe is connected to the converging pipe through a second connector of the T-joint structure;

wherein the raw water pipe is connected to a first terminal and a second terminal of the first connector, and the first probe is inserted into a third terminal of the first connector to contact with water when water is in the raw water pipe; the converging pipe is connected to a first terminal and a second terminal of the second connector, and the second probe is inserted into a third terminal of the second connector to contact with water when water is in the converging pipe.

7. The sensor of claim 1, wherein the coating layer has a thickness of 0.1-1000 nm.

8. A water hardness detection method by using the sensor of claim 1, comprising:

opening the first valve, closing the second valve, injecting raw water into the raw water pipe, locating both the first probe and the second probe in the raw water, and measuring the first potential between the first probe and the second probe;

opening the second valve, closing the first valve, injecting softened water into the softened water pipe, locating the first probe in the raw water, locating the second probe in the softened water, and measuring the second potential between the first probe and the second probe; and determining, by the processor, the water hardness of the softened water according to the potential difference between the first potential and the second potential.

9. The method of claim 8, further comprising:

performing pre-processing on the first potential and the second potential; and inputting into the processor the first potential and the second potential after being subjected to the pre-processing;

wherein the pre-processing comprises impedance transformation matching, linear amplification, level shifting and/or noise processing.

10. The method of claim 8, the controller is further configured to being connecting to a regeneration system of a water softener to control regeneration and maintenance of ion exchange resin in the water softener, and the method further comprises:

turning on, by the controller, the regeneration system of the water softener if the water hardness reaches a preset value.

11. The method of claim 8, wherein the sensor further comprises a displayer, and the method further comprises:

displaying the water hardness of the softened water by the displayer.

* * * * *